United States Patent
Vida

(10) Patent No.: US 7,767,098 B2
(45) Date of Patent: Aug. 3, 2010

(54) METHOD FOR HARVESTING FAT CELLS FROM A FAT-FLUID MIXTURE

(76) Inventor: Vida Tavafoghi Vida, 32 Bodie Rd., Wayne, NJ (US) 07470

( * ) Notice: Subject to any disclaimer, the term of this patent is extended or adjusted under 35 U.S.C. 154(b) by 463 days.

(21) Appl. No.: 10/263,612

(22) Filed: Oct. 3, 2002

(65) Prior Publication Data

US 2004/0067219 A1   Apr. 8, 2004

(51) Int. Cl.
*B01D 43/00* (2006.01)
(52) U.S. Cl. .................. 210/768; 210/767; 210/800; 435/261; 604/378
(58) Field of Classification Search ............... None
See application file for complete search history.

(56) References Cited

U.S. PATENT DOCUMENTS

| | | | | |
|---|---|---|---|---|
| 5,460,621 | A | * | 10/1995 | Gertzman et al. ........... 604/358 |
| 5,469,864 | A | | 11/1995 | Rosenblatt |
| 5,556,391 | A | | 9/1996 | Cercone et al. |
| 5,681,561 | A | * | 10/1997 | Hirshowitz et al. ........ 424/93.7 |
| 6,171,695 | B1 | * | 1/2001 | Fontenot et al. ............ 428/337 |
| 6,269,820 | B1 | * | 8/2001 | Bays ........................... 128/898 |

OTHER PUBLICATIONS

Markey et al, "Autologous Fat Grafting: Comparison of Techniques" (2000) Dermatol Surg, vol. 26, No. 12, pp. 1135-1139.*
Sommer et al, "Current Concepts of Fat Graft Survival: Histology of Aspirated Adipose Tissue and Review of the Literature" (2000) Dermatol Surg, vol. 26, No. 12, pp. 1159-1166.*
Advertisement—Merocel Corporation "Merocel Eye Products," Assumed to be published prior to Oct. 3, 2001.
Advertisement—Merocel Corporation "ENT Products 1994." 1993.
Advertisement—Merocel Corporation "Ophthalmic Products 1994." 1993.
Advertisement—Merocel Corporation "Do Nasal Packings Have You Puzzled?" 1993.
Advertisement—Merocel Corporation "Orthopedic Products." Assumed to be published prior to Oct. 3, 2001.

* cited by examiner

*Primary Examiner*—Allison M Ford
(74) *Attorney, Agent, or Firm*—Nutter McClennen & Fish LLP; Reza Mollaaghababa

(57) ABSTRACT

The present invention teaches a method for separating a fat component of a fluid-fat mixture extracted from a patient. More particularly, the method of invention places a sponge formed of a fluid-absorbing material, such as polyvinyl acetal, in contact with the mixture so as to absorb the fluid component, thereby separating the fat component of the mixture. The separated fat component can then be injected into a selected body portion of the patient.

8 Claims, 2 Drawing Sheets

US 7,767,098 B2

METHOD FOR HARVESTING FAT CELLS FROM A FAT-FLUID MIXTURE

BACKGROUND OF THE INVENTION

The present invention relates generally to method and device for fat transplantation, and more particularly, to a sponge that can be utilized for autologous fat transplantation by injection of aspirated fat cells.

The advent of liposuction over two decades ago has spawned the revolutionary technique of fat transplantation by aspirating fat cells from one portion of a patient body and reintroducing the fat cells to a different portion of the patient's body. Such lipoinjection procedures have spread rapidly through cosmetic and reconstructive surgical communities. A technique typically employed for harvesting fat for lipoinjection is tumescent local anesthesia, a process in which subcutaneous adipose tissue is infiltrated with large volumes of a dilute local anesthesia. The adipose tissue becomes swollen and firm after absorbing the anesthesia, allowing more accurate extraction of the fat cells by employing small diameter cannulas. Because of the infusion of anesthesia fluid into the adipose fluid, the harvested fat cells are mixed with a significant amount of anesthesia fluid when aspirated out of the patient. This fluid has to be discarded without damaging the lipocytes in order to obtain predictable and reliable results when the lipocytes are employed for lipoinjection. In fact, the quality of the results obtained by a lipoinjection procedure is directly related to the purity and viability of the injected fat cells. Thus, the ability to separate the anesthesia fluid from the aspirated fat-fluid mixture is crucial for providing fat cells of suitable quality and quantity for reintroduction into the patient.

A variety of techniques are known for separating the fluid from the fat cells. Some of these techniques include the use of a filter paper, a surgical gauze as a filter, sifters, centrifugation, and separation by gravity. All of these techniques, however, suffer from a number of shortcomings. For example, centrifugation and separation-by-gravity can be time consuming and inefficient.

Accordingly, there is a need for method and device that allow purifying fat for lipoinjection in a more efficient manner.

There is also a need for such a device and method that are cost effective, and can be readily utilized by practitioners.

SUMMARY OF THE INVENTION

In one aspect, the present invention provides a method for separating fat cells from a fat-fluid mixture extracted from a patient by employing a sponge formed of a fluid-absorbing material, such as, polyvinyl acetal, to remove the fluid from the mixture. More particularly, in a method of the invention, the sponge is brought into contact with the extracted fat-fluid mixture, for example, by placing the sponge in a container in which the mixture is disposed, so as to allow the sponge to absorb the fluid component of the mixture. In this manner, the fluid is removed from the mixture, and the remaining fat component is isolated and can be collected. The term "fat component" as used herein refers to the portion of the mixture that is not absorbed by the sponge, and exhibits a substantially higher fat cell density than the original mixture. That is, the fat component may contain some fluid, albeit at much lower density than present in the original mixture. For example, the fat cell density of the fat component can be in a range of about 50% to 100%, and more preferably, in a range of about 80% to 100%. The collected fat can then be injected into a selected body portion of the patient.

In another aspect, a sponge according to the teachings of the invention can include a body formed of a fluid-absorbing material, such as polyvinyl acetal, that extends from a base to a tip. The sponge can have a variety of different shapes and sizes. For example, the sponge can have a substantially pyramidal structure with the base and the tip having substantially rectangular shapes. Alternatively, the sponge can have a substantially conical or a cylindrical structure. Further, while in some embodiments the base has a larger area than that of the tip, in other embodiments the sponge body has a substantially uniform cross-section extending from the base to the tip.

In a related aspect, a sponge of invention has pores with sizes in a range of about 0.2 mm to about 1 mm. Further, the material forming the sponge can include a small amount of a softening agent, such as, glycerin, in order to enhance the fluid absorption properties of the sponge.

In further aspects, a sponge according to the teachings of the invention includes one or more channels formed therein to facilitate the absorption of fluid by the sponge. The channels can extend from the base to the tip, or can originate from a peripheral surface of the sponge. The channels can extend entirely or partially through the sponge body to facilitate the uptake of the fluid from the fat-fluid mixture.

Further understanding of the invention can be obtained by reference to the following description in conjunction with the associated drawings described briefly below.

DETAILED DESCRIPTION OF THE INVENTION

The present invention provides a method of separating fat cells from a mixture of fat and fluid, for example, a fat-fluid mixture extracted from a patient, by employing a sponge, constructed in accordance with the teachings of the invention as discussed in detail below, that exhibits an excellent fluid-absorption property. More particularly, as discussed in detail below, in a method of the invention, such a sponge is brought into contact with the fat-fluid mixture so as to selectively absorb the fluid component of the mixture, thereby allowing harvesting the fat component. In the following discussion, various embodiments of a sponge according to the teachings of the invention that are suitable for practicing the separation method of the invention are presented, and further various steps of such a separation method are described.

Figure 1:
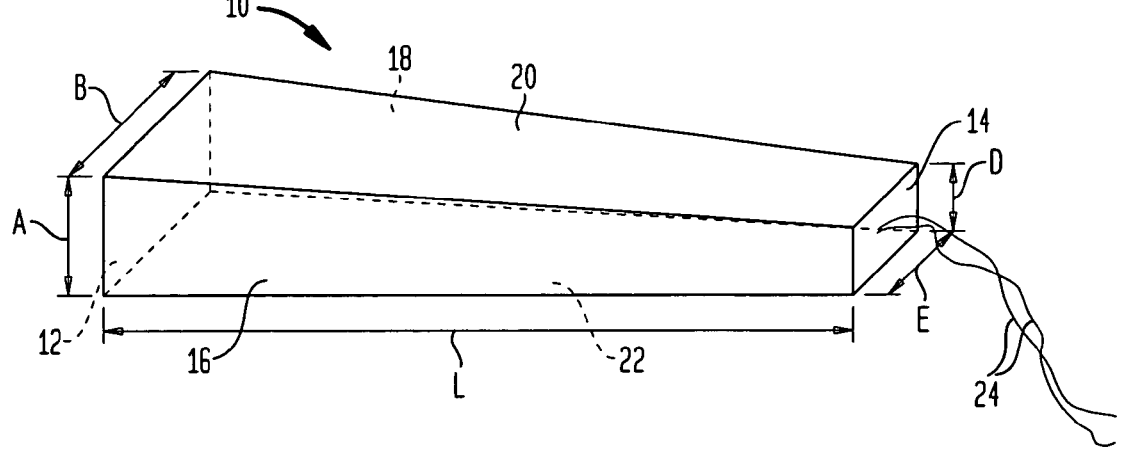
FIG. 1 schematically illustrates a sponge according to the teachings of the invention that can be employed for harvesting fat cells from a mixture of fat and fluid extracted from a patient, FIG. 2 schematically illustrates the use of the sponge of the present invention for removing fluid from a fat-fluid mixture by placing the sponge of FIG. 1 in a syringe in which the fat-fluid mixture is disposed.

FIG. 1 schematically depicts an exemplary sponge 10 according to the teachings of the invention that can be utilized for separating fat from a mixture of fat and fluid extracted from a patient, for example, from a patient's abdomen, hip or thigh. The harvested fat can then be injected into another body portion of the patient, e.g., the patient's face. The exemplary sponge 10, which has a generally pyramidal structure, includes a base 12 and a tip 14 that are separated by a selected distance L. In this embodiment, both the base 12 and the tip 14 are formed by substantially rectangular surfaces having different surface areas. In particular, the base 12 has a surface area that is larger than that of the tip 14.

With continued reference to FIG. 1, the exemplary sponge 10 further includes four peripheral surfaces composed of two side surfaces 16 and 18, a top surface 20 and a bottom surface 22. The peripheral surfaces extend from the base 12 to the tip 14. At least one of the top surface 20 and/or the opposed bottom surface 22 is slanted such that a cross-section of the exemplary sponge 10 on any plane parallel to the base and tip surfaces exhibits a rectangular shape whose area increases continuously from the tip to the base.

The exemplary sponge 10 further includes a plurality of threads 24 coupled to the tip 12 that can be utilized for removing the sponge from a container in which fat-fluid mixture is disposed subsequent to the absorption of the fluid component by the sponge, as described below.

The sponge 10 can have any desired size that is suitable for a particular embodiment of a separation method of the invention. For example, the sponge 10 can be shaped and sized so as to fit within a conventional surgical syringe in which the fat-fluid mixture is disposed. Alternatively, the sponge 10 can be sized to efficiently absorb the fluid component of a fat-fluid mixture disposed in another container. By way of example only, the lengths A and B of the two sides of the rectangular base 12 can be selected to be in a range of about a few millimeters to about tens of centimeters, e.g., A can be 15 mm while B is 6 mm. A similar range can be selected for the lengths E and D of the two sides of the tip 14, e.g, E can be 6 mm while D is 6 mm. The length L of the sponge can also be selected within a wide range of values, e.g., from a few millimeter to tens of centimeter, such as 150 mm.

The sponge 10 can be constructed by utilizing a variety of manufacturing techniques known in the art. In some preferred embodiments of the invention, the sponge 10 is formed of polyvinyl acetal by cross linking polyvinyl alcohol while simultaneously adding air. In some embodiments, a small amount, e.g., less than about 1 percent, of glycerin is added as a softening and wetting agent in order to enhance the fluid absorption properties of the sponge. The sponge 10 can have pores with sizes in a range of about 0.2 mm to about 1 mm. Further, the threads 24 can be formed of nylon. Those having ordinary skill in the art will appreciate that other materials can also be employed for forming the sponge 10 so long as the material exhibits fluid-absorption properties needed for proper functioning of the sponge for separating fat from a fluid-fat mixture.

Figure 2:
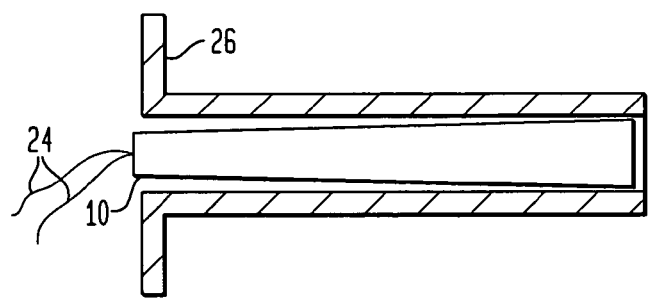

With reference to FIG. 2, in one embodiment of a separation method of the invention, the sponge 10 can be utilized for harvesting fat cells from a mixture of fat and fluid removed from a patient, and more particularly, for small volume fat transfers, as described below. For example, the sponge can be placed, with its base first, into a syringe 26 subsequent to removing the syringe's plunger. A mixture of fat and fluid (not shown), which has been removed from a patient, can then be placed into the syringe over the sponge. The sponge quickly and efficiently absorbs the fluid, leaving behind purified viable fat that can be utilized for injection into the patient. The sponge can be kept in contact with the mixture for a sufficient duration to allow it to absorb a substantial amount of the fluid component, and preferably the entire fluid component. For example, the sponge can be kept in contact with the fluid for a sufficient duration so as to result in saturation of the sponge with the fluid component. In some cases, the remaining fat component may still contain a volume of the fluid. Such a fat component can be further purified by application of an additional sponge of the invention, as discussed below.

The sponge can then be removed from the syringe and the purified fat can be transferred from the syringe to smaller syringes for injection. The volume of fat obtained after purification by the sponge 10 is typically one-third of the volume of fat and fluid originally applied to the syringe in which the sponge is placed. Those having ordinary skill in the art will appreciate that other results can be obtained depending, for example, on the shape and size of a sponge that is utilized and/or duration of the contact of the sponge with the mixture.

Different syringe and sponge sizes can be utilized. Further, the fat can be separated from the fat-fluid mixture by repeated application of a sponge of the invention, such as the above sponge 10, to the same mixture. That is, subsequent to an initial application of the sponge to the mixture, and removal of a selected amount of the fluid, another sponge can be applied to the partially purified sample to remove additional fluid, thereby enhancing the purity of the harvested fat. This process can be repeated as many times as needed to obtain a desired purity of the harvested fat.

A separation method of the invention provides distinct advantages over conventional fat purification techniques. For example, to evaluate efficacy of a method of the invention for fat purification in comparison with the separation-by-gravity technique, fat was passively separated from a mixture of fat and fluid over a four-day period by employing separation-by-gravity. A sponge of the invention was then placed in the gravity-purified fat. The sponge absorbed enough fluid from the gravity-purified fat to reduce its volume by approximately 25%. That is, the sponge substantially improved the purification of the fat that was harvested by utilizing the separation-by-gravity technique. Moreover, the fat cells purified by the sponge of the invention were examined and found to be completely normal and unaffected by the purification process. Thus, the separation method of the invention is superior to passive separation techniques.

Further, a sponge of the invention, for example, the exemplary sponge 10, is simple to use, highly effective for fat purification, and can be provided in a sterile, prepackaged form for easy storage in an office or a surgical facility.

Fat obtained through a method of the invention can be employed to obtain the most concentrated and viable fat grafts to date, thereby enhancing predictability and success of cosmetic and surgical procedures. For example, areas that are conventionally classified as poor recipient sites can become viable candidates for lipoinjection by utilizing fat harvested by employing the method of the invention. Hence, the method of the invention can significantly lower the incidence of graft loss or partial take, thus obviating the need to overtreat. This is especially advantageous when treating a patient's face.

Figure 3:
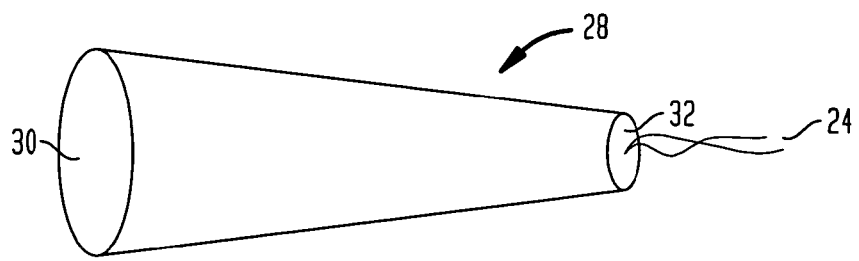
FIG. 3 is another sponge according to the teachings of the invention having a substantially conical body.
Figure 4:
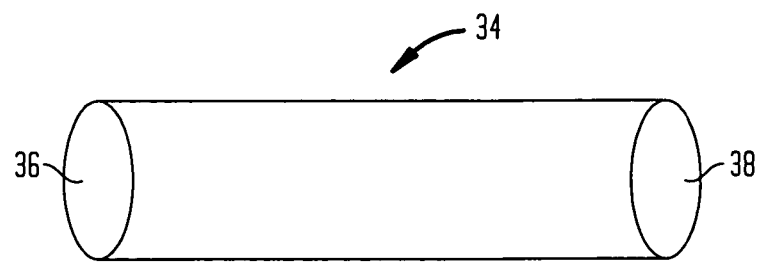
FIG. 4 is another sponge according to the teachings of the invention having a cylindrical structure, FIG. 5A schematically illustrates a sponge of the invention having a generally pyramidal structure and having a plurality of channels therein, FIG. 5B schematically illustrates another sponge according to the teachings of the invention having a generally conical structure and having a plurality of channels therein, and FIG. 6 schematically illustrates the use of a sponge according to the teachings of the invention for harvesting fat cells from a fat-fluid mixture by placing the sponge in a container in contact with a fat-fluid mixture disposed in the container.

It should be understood that the structure of a sponge according to the teachings of the invention is not limited to that described above. In fact, a sponge of the invention can be made of a fluid-absorbing material, such as polyvinyl acetal, in a variety of shapes and sizes to harvest fat cells from a mixture of fat and fluid. For example, FIG. 3 schematically illustrates another sponge 28 according to the teachings of the invention that is formed of a generally conical body that extends from a substantially circular base 30 to a substantially circular tip 32. Similar to the previous sponge 10, the base 30 of this sponge has a larger cross-sectional area than that of the tip 32. Further, one or more threads 24, e.g., nylon threads, can be optionally attached to the tip 32 to facilitate removal of the sponge from a container, e.g., a syringe, By way of another example, FIG. 4 schematically illustrates another sponge 34 according to the teachings of the invention that includes a substantially cylindrical body that extends from a circular base 36 to a circular tip 38. Unlike the above embodiments, the sponge 34 exhibits a substantially uniform cross-section extending from the base 36 to the tip 38. The cross-sectional area of the sponge 34 in a plane perpendicular to a longitudinal axis extending from the base to the tip, and its length can have a variety of sizes selected, for example, based on the size of the container in which the sponge is placed for harvesting fat. For example, the cross-sectional area of the sponge 34 can be in a range of about 5 $mm^2$ to about 100 $cm^2$ while the length of the sponge 34 can take values in a range from about 5 mm to about 50 cm. Those having ordinary skill in the art will appreciate that other sizes can also be utilized.

Figure 5A:
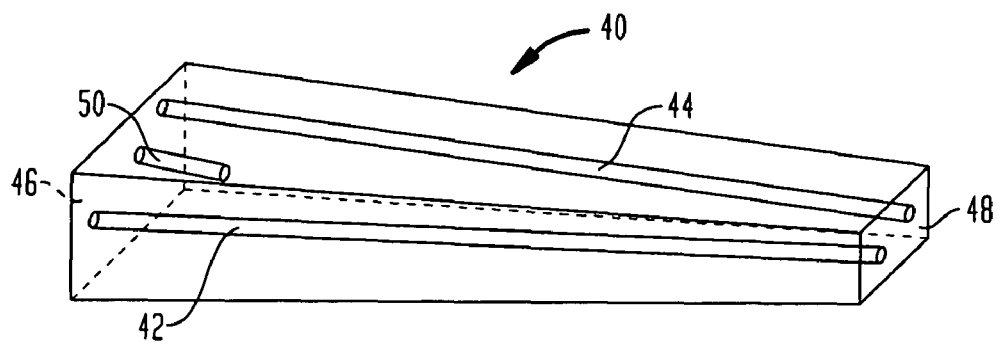

In other aspects, a sponge of the invention can include one or more channels therein for facilitating absorption of fluid by the sponge. For example, FIG. 5A illustrates a sponge 40 of the invention that exhibits a generally pyramidal structure and further includes two channels 42 and 44 that extend from its base 46 to its tip 48, and a channel 50 that originates at its base and partially penetrates the sponge body. Those having ordinary skill in the art will appreciate that one or more channels that originate from any of the peripheral surfaces of the sponge and extend either to the base or the tip, or one of the other peripheral surfaces, or extend partially into the sponge body can also be provided.

Figure 5B:
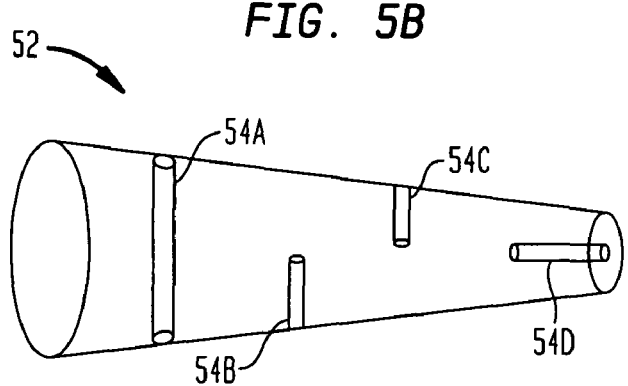

By way of another example, FIG. 5B schematically illustrates another sponge 52 of the invention having a generally conical body in which a plurality of channels 54a, 54b, 54c, and 54d, herein collectively referred to as channels 54, are formed. While the channel 54a spans the entire cross-section of the sponge 52, the channels 54b, 54c, and 54d extend only partially through the sponge body.

Figure 6:
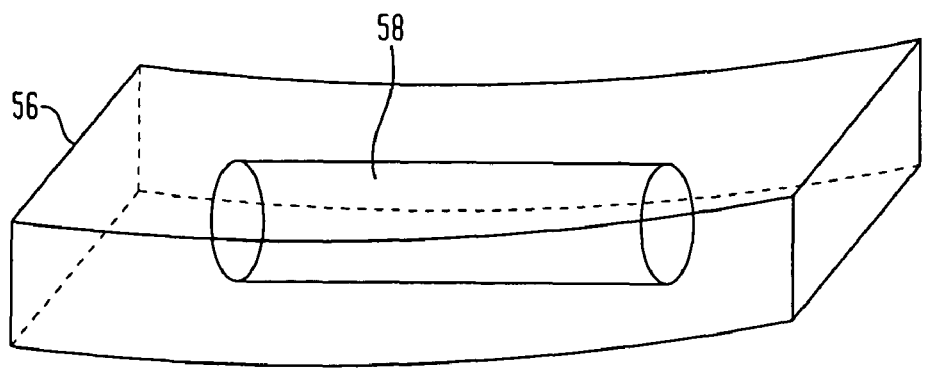

As discussed above, a sponge of the invention can be employed to remove fluid from a mixture of fat and fluid extracted from a patient by utilizing, for example, a tumescent local anesthesia technique. For example, according to one embodiment described above, a sponge of the invention can be inserted into a syringe in which a fat-fluid mixture is disposed in order to remove fluid from the fat. It should, however, be understood that a method of the invention can be practiced by placing a fat-fluid mixture in any desired container, e.g., syringes of different sizes or a dish, and utilizing a sponge of the invention that is sized and shaped in order to fit in the container to remove a volume of the fluid from the mixture. By way of example, FIG. 6 illustrates a container 56 in which a cylindrical sponge 58 of the invention can placed to absorb fluid from a fat-fluid mixture extracted from a patient and disposed in the container.

In another aspect, the invention provides a medical kit for separating fat from a fat-fluid mixture extracted from a patient. Such a medical kit can include a sterile sponge according to the teachings of the invention, such as those described above, that is formed of a fluid-absorbing material, e.g., polyvinyl acetal, and a sterile container, e.g., a syringe from which the plunger is removed, in which a fat-fluid mixture extracted from a patient can be disposed. Further, the medical kit can include a sterile device, e.g., a syringe, that can be employed to collect the separated fat component.

Those having ordinary skill in the art will appreciate that various modifications can be made to the above embodiments without departing from the scope of the present invention. For example, the method of the invention can be practiced by employing a sponge made in various sizes and shapes in accordance with the teachings of the invention.

What is claimed is:

1. A method for separating fat cells from a fat-fluid mixture, the method comprising the steps of:
   extracting a fat-fluid mixture from a human subject,
   providing one or more sponges formed of a fluid-absorbing material having pores with sizes in a range of about 0.2 mm to about 1 mm, and
   separating the fat component from the fat-fluid mixture without centrifugation by placing the one or more sponges in at least partial contact with the mixture so as to selectively absorb at least a portion of the fluid component of the mixture, wherein absorption of the fluid component by said one or more sponges results in a separated fat component exhibiting a fat cell density in a range of about 50% to 100% and which is suitable for injection into a selected portion of a human subject, and
   collecting the separated fat component.

2. The method of claim 1, wherein the fluid-absorbing material is polyvinyl acetal.

3. The method of claim 1, further comprising injecting the separated fat component into a selected body portion of the human subject.

4. The method of claim 1, wherein the step of placing the one or more sponges in at least partial contact with the mixture comprises disposing the fat-fluid mixture in a container and placing the one or more sponges in the container so as to have contact with the mixture.

5. The method of claim 1, wherein the volume of the separated fat component is about one-third of the volume of the fluid-fat mixture.

6. The method of claim 4, wherein the step of collecting the separated fat component comprises removing the one or more sponges from the container and collecting the separated fat component.

7. The method of claim 6, further comprising injecting the collected fat component into a selected body part of the human subject.

8. The method of claim 1, wherein said separated fat component exhibits a fat cell density in a range of about 80% to about 100%.

* * * * *